US006528522B2

(12) United States Patent
Shih et al.

(10) Patent No.: US 6,528,522 B2
(45) Date of Patent: Mar. 4, 2003

(54) SUBSTITUTED IMIDAZOLES AS DUAL HISTAMINE $H_1$ AND $H_3$ AGONISTS OR ANTAGONISTS

(75) Inventors: Neng-Yang Shih, North Caldwell, NJ (US); Robert G. Aslanian, Rockaway, NJ (US); John J. Piwinski, Clinton Township, NJ (US); Andrew T. Lupo, Jr., Emerson, NJ (US); Adriano Afonso, West Caldwell, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 09/954,863

(22) Filed: Sep. 18, 2001

(65) Prior Publication Data

US 2002/0082272 A1 Jun. 27, 2002

Related U.S. Application Data

(60) Provisional application No. 60/234,038, filed on Sep. 20, 2000.

(51) Int. Cl.[7] .................... A61K 31/435; C07D 401/12; C07D 401/14; A61P 11/06; A61P 25/00
(52) U.S. Cl. ...................... 514/290; 514/292; 514/400; 514/399; 546/93; 546/81; 548/300.1; 548/338.1
(58) Field of Search .................. 546/93, 81; 548/300.1; 514/290, 292, 400

(56) References Cited

U.S. PATENT DOCUMENTS

| 4,767,778 A | 8/1988 | Arrang et al. |
| 5,352,707 A | 10/1994 | Pompni et al. |
| 5,869,479 A | 2/1999 | Kreutner et al. |

FOREIGN PATENT DOCUMENTS

| EP | 0448 765 B1 | 3/1990 |
| EP | 0 420 396 B1 | 7/1990 |
| WO | WO 93/01812 | 2/1993 |
| WO | WO 93/12093 | 6/1993 |
| WO | WO 95/14007 | 5/1995 |
| WO | WO 96/29315 | 9/1996 |
| WO | WO 98/58646 | 12/1998 |

OTHER PUBLICATIONS

Sasse, A., Bioorganic & Medicinal Chemistry, vol. 8, (Partial) Agonist/ Antagonist Properties of Novel Diarylalkyl Carbamates on Histamine H3 Receptors, pp. 1139–1149 (2000).
Stark, H., Drugs of the Future, vol. 21(5) Developments of Histamine H3–receptor antagonists, pp 507–520 (1996).
Howson, Bioorganic & Medicinal Chemistry Letters, Two Novel, Potent and Selective Histamine H3 Receptor Agonists, vol. 2, pp. 77–78, 1992.
Stark, J. Med. Chem., Novel Carbamates as Potent Histamine H3 Receptor Antagonists with High in Vitro and Oral In Vivo Activity, 39, pp. 1157–1163.
Sasse, Bioorganic & Medicinal Chemistry, (Partial) Agonist/ Antagonist Properties of Novel Diarylalkyl, vol. 8 (2000) pp. 1139–1149.
Bagley, J. Med. Chem. 1991, New 1–(Heterocyclylalkyl)–4–(Propionanilido)–4–Piperidinyl, 34, pp 827–941.
Huls, Bioorganic & Medicinal Chemistry Letters, Diphenylmethyl Ethers: Synthesis and Histamine, vol. 6, No. 16, pp. 2013–2018, 1996.
Buschauer, J. Med. Chem. 1989, Synthesis and in Vitro Pharmacology of Arpromidine, 32, pp 1963–1970, 1989.
Schulze, Arch. Pharm. (Weinheim), Synthese und kombinierte H1/H2–antagonistische, vol. 327, pp. 455–462, 1994.
Schulze, European Journal of Pharmaceutical Sciences, Combined histamine H1/H2 receptor antagonists, vol. 6, pp. 177–186, 1998.
van der Goot, Eur J. Med. Chem., Isothiourea analogues of histamine as potent agonists, vol. 27, pp. 511–517, 1992.
Walczynski, II Farmaco, Non–imidazole histamine H3 ligands, Vo. 54, pp. 684–694, 1999.
Brown, Br. J. Pharmac., Pharmacological studies with SK & F 93944, vol. 87, pp. 569–578, 1986.
West, Molecular Pharmacology, Identificatin of Two H3–Histamine Receptor Subtypes, vol. 38, pp. 610–613, 1990.
Clapham, Brit. J. Pharm. Suppl., Ability of the Selective Histamine H3 Receptor Antagonist, vol. 110, pp. Abs. 65P, 00/00, 1993.
Yokoyama, European Journal of Pharmacology, Effect of Thioperamide, vol. 234, pp 129–133, 1993.
Schlicker, Br. J. Pharmacol., Novel Histamine H3 Receptor Antagonists, vol. 112, pp. 1043–1048, 1994.
Leurs, Progre. Drug. Res., The Histamine H3–Receptor, vol. 39, pp. 127–165, 00/00, 1992.
Lipp, Histamine Receptor, Pharmacochemistry of H3–Receptors, pp. 57–72, 00/00, 1992.
Stark, European Journal of Pharmaceutical Sciences, New potent Histamine H3–Receptor vol. 3, pp. 95–104, 1995.

*Primary Examiner*—Evelyn Mei Huang
(74) *Attorney, Agent, or Firm*—Palaiyur S. Kalyanaraman

(57) ABSTRACT

The present invention discloses novel substituted imidazole compounds which have $H_3$ receptor antagonist activity or dual histamine-$H_1$ and $H_3$ receptor antagonist activity as well as methods for preparing such compounds. In another embodiment, the invention discloses pharmaceutical compositions comprising such imidazoles as well as methods of using them to treat allergy, congestion, inflammatory and CNS-related diseases and others.

19 Claims, No Drawings

SUBSTITUTED IMIDAZOLES AS DUAL HISTAMINE H₁ AND H₃ AGONISTS OR ANTAGONISTS

FIELD OF THE INVENTION

The present invention relates to novel substituted imidazole compounds having valuable pharmacological properties, especially against inflammatory diseases and allergic conditions. Compounds of this invention are antagonists of the histamine receptors. Some are antagonists of the histamine-$H_3$ receptors. Some are antagonists of both the $H_1$ and $H_3$ receptors, in other words dual $H_1$ and $H_3$ receptor antagonists. The invention disclosed in this application claims priority from provisional application, Ser. No. 60/234,038 filed Sep. 20, 2000, and is related to that in pending provisional applications, Ser. No. 60/234,040, Ser. No. 60/234,039, and Ser. No. 60/234,053, all filed on Sep. 20, 2000.

BACKGROUND OF THE INVENTION

The histamine receptors, $H_1$, $H_2$ and $H_3$ are well-identified forms. The $H_1$ receptors are those that mediate the response antagonized by conventional antihistamines. $H_1$ receptors are present, for example, in the ileum, the skin, and the bronchial smooth muscle of humans and other mammals. A well-known antagonist of $H_1$ receptors is loratadine, commercially available under the tradename CLARITIN® from Schering-Plough Corporation, Madison, N.J. Through $H_2$ receptor-mediated responses, histamine stimulates gastric acid secretion in mammals and the chronotropic effect in isolated mammalian atria.

$H_3$ receptor sites are found on sympathetic nerves, where they modulate sympathetic neurotransmission and attenuate a variety of end organ responses under control of the sympathetic nervous system. Specifically, $H_3$ receptor activation by histamine attenuates nonepinephrine outflow to resistance and capacitance vessels, causing vasodilatation.

U.S. Pat. No. 4,767,778 (Arrang et al.) discloses certain imidazoles that behave as agonists of the $H_3$ receptors in rat brain. European Patent Application No. 0 420 396 A2 (Smith Kline & French Laboratories Limited) and Howson et al. (Bioorg. & Med. Chem. Letters, (1992), Vol. 2 No.1, pp. 77–78) describe imidazole derivatives having an amidine group as $H_3$ agonists. Van der Groot et al. (Eur. J. Med. Chem. (1992) Vol. 27, pp. 511–517) describe isothiourea analogs of histamine as potent agonists or antagonists of the histamine-$H_3$ receptor, and these isothiourea analogs of histamine overlap in part with those of the two references cited above. Clapham et al. ["Ability of Histamine-$H_3$ Receptor Antagonists to Improve Cognition and to Increase Acetylcholine Release in vivo in the Rat", British Assn. for Psychopharmacology, July 25–28 (1993), reported in J. Psychopharmacol. (Abstr. Book), A17] describe the ability of histamine-$H_3$ receptor antagonists to improve cognition and to increase release of acetylcholine in vivo in the rat. Clapham et al. ["Ability of the selective Histamine-$H_3$ Receptor Antagonist Thioperamide to improve Short-term Memory and Reversal Learning in the Rat", Brit. J. Pharm. Suppl., 1993, 110, Abstract 65P] present results showing that thioperamide can improve short-term memory and reversal learning in the rat and implicate the involvement of $H_3$ receptors in the modulation of cognitive function. Yokoyama et al.. ["Effect of Thioperamide, a Histamine-$H_3$ Receptor Antagonist, on Electrically Induced Convulsions in Mice", Eur. J. Pharmacol., (1 993), Vol. 234, pp. 129–133] report how thioperamide decreased the duration of each phase of convulsion and raised the electroconvulsive threshold, and go on to suggest that these and other findings support the hypothesis that the central histaminergic system is involved in the inhibition of seizures. International Patent Publication No. WO 9301812-A1 (SmithKline Beecham PLC) describes the use of S-[3-(4(5)-imidazolyl)propyl] isothiourea as a histamine-$H_3$ antagonist, especially for treating cognitive disorders, e.g. Alzheimer's disease and age-related memory impairment. Schlicker et al. ["Novel Histamine-$H_3$ Receptor Antagonists: Affinities in an $H_3$ Receptor Binding Assay and Potencies in Two Functional $H_3$ Receptor Models", British J. Pharmacol., (1994), Vol. 112, 1043–1048] describe a number of imidazolylalkyl compounds wherein the imidazolylalkyl group is bonded to a guanidine group, an ester group, an amide group, a thioamide group and a urea group, and compared these to thioperamide. Leurs et al.. ["The Histamine-$H_3$-receptor: A Target for Developing New Drugs", Progr. Drug Res. (1992), Vol. 39, pp.127–165] and Lipp et al.. ["Pharmacochemistry of $H_3$-receptors" in The Histamine Receptor, eds.: Schwartz and Haas, Wiley-Liss, New York (1992), pp. 57–72] review a variety of synthetic $H_3$ receptor antagonists, and Lipp et al. (ibid.) have proposed the necessary structural requirements for an $H_3$ receptor antagonist.

WO 95/14007 claims $H_3$ receptor antagonists of the formula

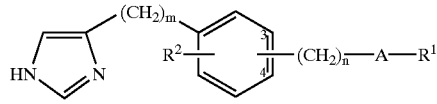

wherein A, m, n, $R^1$ and $R^2$ are defined therein. The compounds are disclosed as being useful for treating various disorders, in particular such caused by allergy-induced responses.

WO 93/12093 discloses imidazolylmethyl piperazines and diazepines as $H_3$ antagonists. U.S. patent application, Ser. No. 08/965,754, filed Nov. 7, 1997, discloses imidazolylalkyl substituted heterocyclic ring compounds as $H_3$ receptor antagonists. U.S. patent application, Ser. No. 08/966,344, filed Nov. 7, 1997, discloses phenylalkylimidazoles as $H_3$ receptor antagonists.

WO 96/29315 (PCT/FR96/00432) discloses certain N-imidazolylalkyl compounds containing phenyl moieties attached.

Also disclosing $H_3$ receptor antagonists are: H. Stark et al, Eur. J. of Pharmaceutical Sciences (1995) 3, 95–104; H. Stark et al, J. Med. Chem., (1996) 39, 1157–1163; H. Stark et al, Arch. Pharm. Pharm. Med. Chem., (1998) 331, 211–218; and A. Sasse et al, Bioorganic & Medicinal Chem., (2000) 8, 1139–1149.

Reference is also made to J. R. Bagley et al.. Journal of Medicinal Chemistry, (1991), Vol. 34, 827–841, which discloses, among others, N-(imidazolylalkyl) substituted cyclic amine compounds useful as analgesics such as the amine compound with the formula:

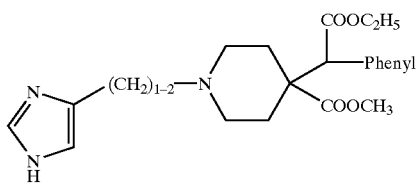

Pending U.S. patent application, Ser. No. 09/173,642, filed Oct. 16, 1998 (R. Wolin et al.) U.S. Pat. No. 6,133,291, discloses N-(imidazolylalkyl) substituted cyclic amine compounds having $H_3$ antagonist activity.

A. Huls et al., *Bioorg. & Med. Chem. Letters,* 6 (1996), 2013–2018 disclose imidazole compounds containing diphenyl ether moieties as $H_3$ receptor antagonists. The compounds are additionally disclosed to have $H_1$ receptor antagonist activity. An example compound from that publication is:

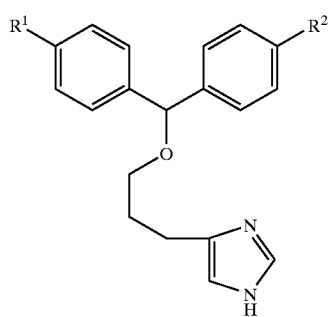

where $R_1$ and $R_2$ are defined therein.

A. Buschauer, *J. Med. Chem.,* 32 (1989), 1963–1970 disclose, among others, $H_2$ receptor antagonists of the type:

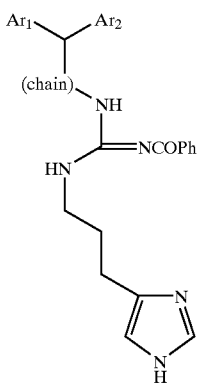

where $Ar_1$ and $Ar_2$ may be phenyl and/or pyridyl. EPO 448,765 A1 (published Mar. 30, 1990) discloses neuropeptide-Y antagonist imidazoles of the type:

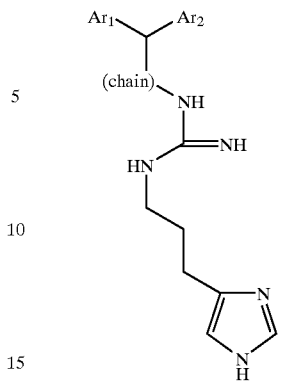

where $Ar_1$ and $Ar_2$ may be phenyl and/or pyridyl.

WO 98-58646 (assigned to Novo Nordisk A/S) discloses somatostatin SSTR4 receptor antagonist compounds of the type:

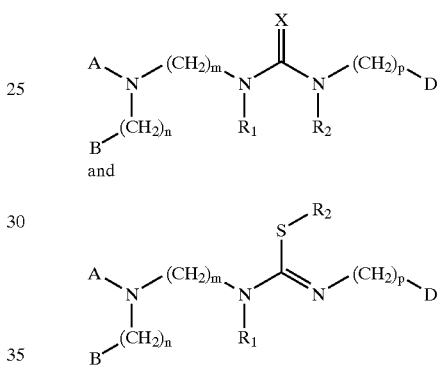

wherein m is 2–6; n is 1–3; p is 1–6; $R_1$ and $R_2$ are independently H or C1–C6 alkyl optionally substituted with halogen, amino, hydroxy, alkoxy or aryl; X is S, O, NH, NCOPH or N(CN); A is aryl optionally substituted with halogen, amino, hydroxy, nitro, C1–C6 alkyl, C1–C6 alkoxy, or aryl; and B and D are independently aryl optionally substituted with halogen, amino, hydroxy, C1–C6 alkyl, C1–C6 alkoxy, or aryl.

Compounds have been reported in the literature as having activity against both $H_1$ and $H_2$ receptors, i.e. dual antagonists against $H_1$ and $H_2$ receptors. Thus, for example, F. Schulze et al., *European J. of Pharmaceutical Sciences,* 6 (1998), 177–186 report combined $H_1/H_2$ receptor antagonists. Other references in this category include F. Schulze et al., *Arch. Pharm. (Weinheim),* 327 (1994), 455–462; C. Wolf et al., *Arch. Pharm. Pharm. Med. Chem.,* 329 (1996), 87–94; and C. Wolf et al., *European J. of Pharmaceutical Sciences,* 6 (1998),177–186. Non-imidazole histamine $H_3$ ligands, particularly substituted benzothiazole derivatives as $H_3$ antagonists and $H_1$ blocking activities have been reported by K. Walczynski et al, *Il Farmaco,* 54 (1999), 684–694.

It would be useful to have compounds which are therapeutically effective as antagonists of both the $H_1$ and $H_3$ histamine receptors. The only such reported activity has been through a combination of two different chemical entities, one showing activity against $H_1$ receptors and the other showing activity against $H_3$ receptors. Thus, for example, U.S. Pat. No. 5,869,479 (issued Feb. 9, 1999 to Schering Corporation) discloses the combination of a histamine-$H_1$ receptor antagonist and a histamine-$H_3$ receptor antagonist for the treatment of allergy-induced airway responses.

Pending provisional patent application, Ser. No.60/234, 040, filed Sep. 20, 2000, discloses novel imidazole compounds having $H_3$ as well as dual $H_1$ and $H_3$ antagonist activity. The compounds disclosed therein have general formula in which an imidazole is linked to two cyclic moieties via intermediary moiety or moieties which intermediary moiety or moieties are acyclic.

Pending provisional patent application, Ser. No. 60/234, 039, filed Sep. 20, 2000, discloses novel imidazole compounds having $H_3$ as well as dual $H_1$ and $H_3$ antagonist activity. The compounds disclosed therein have general formula in which an imidazole is linked to two cyclic moieties via intermediary moiety or moieties which intermediary moiety or moieties are acyclic..

Pending provisional patent application, Ser. No. 60/234, 053, filed Sep. 20, 2000, discloses novel imidazole compounds having $H_3$ as well as dual $H_1$ and $H_3$ antagonist activity. The compounds disclosed therein have general formula in which an imidazole is linked to a tricyclic moiety via intermediary moiety or moieties at least one of which intermediary moiety or moieties is a cyclic moiety.

It would be a welcome contribution to the art to have novel substituted imidazole compounds.

It would be useful to have novel imidazoles showing activity against $H_3$ receptors.

It would be useful to have novel substituted imidazoles showing activity against both $H_1$ and $H_3$ receptors.

It would be useful to have novel substituted imidazoles showing activity against both $H_1$ and $H_3$ receptors.

This invention provides just such a contribution by providing novel substituted imidazole compounds having $H_3$ as well as dual $H_1$ and $H_3$ antagonist activity.

SUMMARY OF THE INVENTION

In one embodiment, this invention provides novel substituted imidazole compounds having $H_3$ antagonist activity as well as dual $H_1$ and $H_3$ antagonist activity. The inventive compounds are substituted imidazoles wherein the imidazole is linked to a tricyclic moiety via intermediary moiety or moieties which intermediary moiety or moieties are acyclic. The compounds have the general structure shown in Formula I:

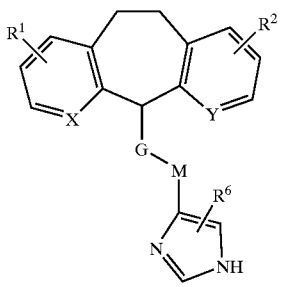

Formula 1 wherein

G is selected from the group consisting of —$(CH_2)_v$—$NR^3$—, —$(CH_2)_v$—O—, —$(CH_2)_v$—$S(O)_z$—, —$(CH_2)_v$—$NR^3$—$C(NR^4)$—$NR^3$—, —$(CH_2)_v$—O—$C(O)NR^3$—, —$(CH_2)_v$—$NR^3C(O)NR^3$—, —$(CH_2)_v$—$NR^3C(O)O$—, —$(CH_2)_v$—$NR^3C(O)$—, —$(CH_2)_vC(O)NR^3$—;

M is a branched or unbranched alkyl group consisting of 1–6 carbon atoms, or a branched or unbranched alkenyl group consisting of 2–6 carbon atoms;

X and Y are independently selected from the group consisting of N, CH or N-oxide;

$R^1$ and $R^2$ may each number 1–4 and are independently selected from the group consisting of H, halogen, lower alkyl, lower alkoxy, polyhalo lower alkoxy, OH, $CF_3$, $NH_2$, NHC(O)alkyl, CN or $NO_2$;

$R^3$ is independently selected from the group consisting of H, lower alkyl, substituted or unsubstituted phenyl, substituted or unsubstituted benzyl, or a group of the formula:

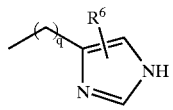

$R^4$ is selected from the group consisting of H, CN, $CO_2R^5$;

$R^5$ is selected from the group consisting of lower alkyl and substituted or unsubstituted benzyl;

$R^6$ is selected from the group consisting of H or lower alkyl;

q is 2–5;

v is 0–6; and z is 0, 1 or 2.

When used herein, the following terms have the given meanings:

lower alkyl (including the alkyl portions of lower alkoxy)—represents a straight or branched, saturated hydrocarbon chain having from 1 to 6 carbon atoms, preferably from 1 to 4;

aryl—represents a carbocyclic group having from 6 to 14 carbon atoms and having at least one benzenoid ring, with all available substitutable aromatic carbon atoms of the carbocyclic group being intended as possible points of attachment. Preferred aryl groups include 1-naphthyl, 2-naphthyl and indanyl, and especially phenyl and substituted phenyl;

cycloalkyl—represents a saturated carbocyclic ring having from 3 to 8 carbon atoms, preferably 5 or 6, optionally substituted.

heterocyclic—represents, in addition to the heteroaryl groups defined below, saturated and unsaturated cyclic organic groups having at least one O, S and/or N atom interrupting a carbocyclic ring structure that consists of one ring or two fused rings, wherein each ring is 5-, 6- or 7-membered and may or may not have double bonds that lack delocalized pi electrons, which ring structure has from 2 to 8, preferably from 3 to 6 carbon atoms, e.g., 2- or 3-piperidinyl, 2- or 3-piperazinyl, 2- or 3-morpholinyl, or 2- or 3-thiomorpholinyl;

halogen—represents fluorine, chlorine, bromine and iodine;

heteroaryl—represents a cyclic organic group having at least one O, S and/or N atom interrupting a carbocyclic ring structure and having a sufficient number of delocalized pi electrons to provide aromatic character, with the aromatic heterocyclic group having from 2 to 14, preferably 4 or 5 carbon atoms, e.g., 2-, 3- or 4-pyridyl, 2- or 3-furyl, 2-or 3-thienyl, 2-, 4- or 5-thiazolyl, 2- or 4-imidazolyl, 2-, 4- or 5-pyrimidinyl, 2-pyrazinyl, or 3- or 4-pyridazinyl, etc. Preferred heteroaryl groups are 2- , 3- and 4-pyridyl; Such heteroaryl groups may also be optionally substituted.

The term "substituted", unless otherwise defined, refers to chemically suitable substitution with moieties such as, for example, alkyl, alkoxy, —$CF_3$, halogen or aryl.

Furthermore, the term "alkyl", when chemically suitable, also includes alkylene and related moieties. Thus, for example, the above-described definitions for G and V, could also include moieties such as, for example, ethylene, butylene, —CH$_2$—CH(CH$_3$)—, —CH$_2$—C(=CH$_2$)—, and the like.

Also included in the invention are tautomers, enantiomers and other optical isomers of compounds of Formula I, as well as pharmaceutically acceptable salts and solvates thereof.

A further feature of the invention is pharmaceutical compositions containing as active ingredient a compound of Formula I (or its salt, solvate or isomers) together with a pharmaceutically acceptable carrier or excipient.

The invention also provides methods for preparing compounds of Formula I, as well as methods for treating diseases such as, for example, inflammation, allergy, diseases of the GI-tract, cardiovascular disease, or disturbances of the central nervous system as well as allergy-induced airway (e.g., upper airway) responses, nasal congestion and obesity. The methods for treating comprise administering to a mammalian patient (including humans and animals) suffering from said disease or diseases a therapeutically effective amount of a compound of Formula I, or pharmaceutical compositions comprising a compound of Formula I.

DETAILED DESCRIPTION OF THE INVENTION

In one embodiment, the present invention provides novel imidazole compounds of Formula I:

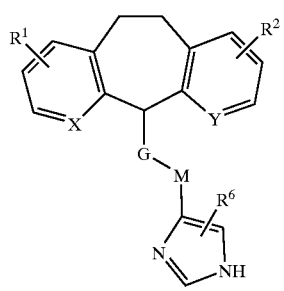

where the various symbols are as defined above. Representative compounds of the invention which exhibit exemplary H$_3$ antagonist activity are listed below.

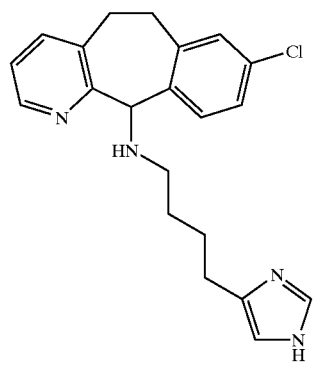

-continued

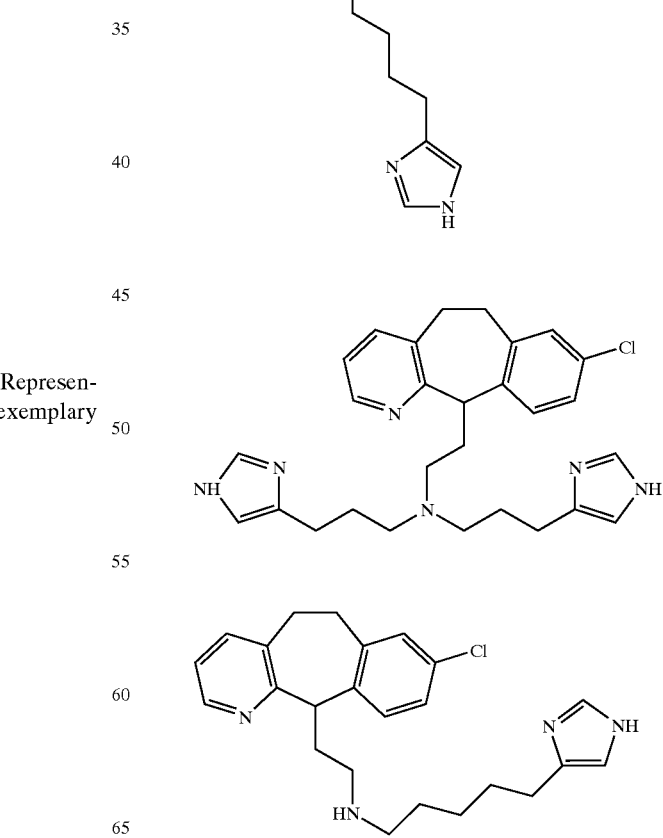

-continued

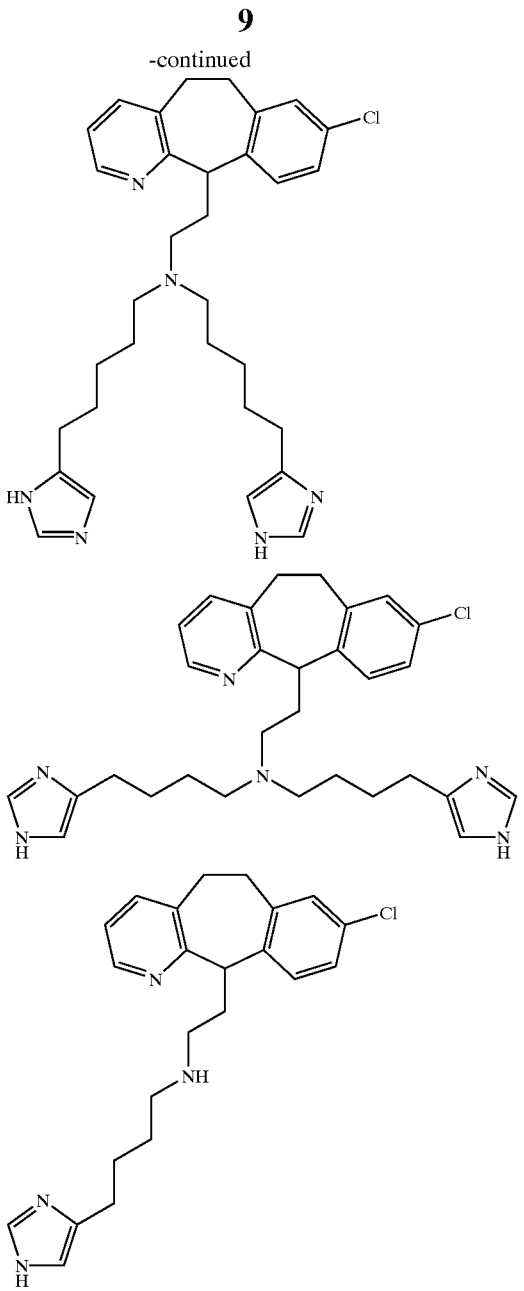

Some examples of compounds exhibiting both $H_1$ and $H_3$ activity include:

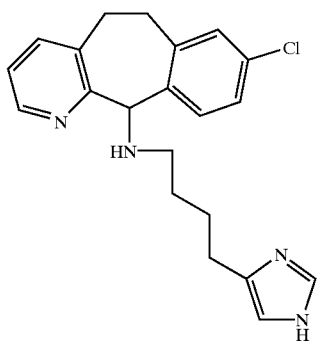

-continued

The compounds of the invention are basic and form pharmaceutically acceptable salts with organic and inorganic acids. Examples of suitable acids for such salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those skilled in the art. The salts are prepared by contacting the free base form with a sufficient amount of the desired acid to produce a salt in the conventional manner. The free base forms may be regenerated by treating the salt with a suitable dilute aqueous base solution such as dilute aqueous sodium hydroxide, potassium carbonate, ammonia and sodium bicarbonate. The free base forms differ from their corresponding salt forms somewhat in certain physical properties, such as solubility in polar solvents, but the salts are otherwise equivalent to their corresponding free base forms for purposes of this invention.

Depending upon the substituents on the inventive compounds, one may be able to form salts with bases too. Thus, for example, if there are carboxylic acid substituents in the molecule, salts may be formed with inorganic as well as organic bases such as, for example, NaOH, KOH, $NH_4OH$, tetraalkylammonium hydroxide, and the like.

As stated earlier, the invention includes tautomers, enantiomers and other stereoisomers of the compounds also. Thus, as one skilled in the art knows, certain imidazole compounds may exist in tautomeric forms. Such variations are contemplated to be within the scope of the invention.

Another embodiment of the invention discloses a method of making the substituted imidazoles disclosed above. The compounds may be prepared by several processes well known in the art. In one method, the imidazole part (designated "the left side component" herein for simplicity purposes) and the tricyclic part (designated "the right side component" herein for simplicity purposes) may be prepared separately. The left side component and the right side component may contain reactive moieties attached to them which moieties are suitable to be reacted with each other under appropriate reaction conditions. Thus, for example, the left side component may contain a carboxylic acid moiety, and the right side component may have an amine moiety. Under appropriate reaction conditions, the two components may be reacted together whereby an imidazole containing a tricyclic alkyl moiety linked through an extended amide chain is obtained. Other substituted imidazoles may similarly be prepared.

Isolation of the compound at various stages of the reaction may be achieved by standard techniques such as, for example, filtration, evaporation of solvent and the like. Purification of the product, intermediate and the like, may also be performed by standard techniques such as recrystallization, distillation, sublimation, chromatography, conversion to a suitable derivative which may be recrystallized and converted back to the starting compound, and the like. Such techniques are well known to those skilled in the art.

The thus prepared compounds may be analyzed for their composition and purity as well as characterized by standard analytical techniques such as, for example, elemental analysis, NMR, mass spectroscopy, and IR spectra.

The inventive compounds can readily be evaluated to determine activity at both $H_1$ and $H_3$ receptors by known methods, such as, for example, E. A. Brown et al, *British J. Pharm.*, (1986) Vol. 80, 569 . $H_3$ activity may be determined by, for example, the guinea pig brain membrane assay and the guinea pig neuronal ileum contraction assay, both of which are described in U.S. Pat. No. 5,352,707. Another useful assay for $H_3$ activity utilizes rat brain membranes and is described by West et al., ("Identification of Two $H_3$-Histamine Receptor Subtypes", *Molecular Pharmacology*, (1990), Vol. 33, 610–613. Several of the present compounds were found to have high $H_1$ and $H_3$ antagonist activity which is discussed more in the EXAMPLES section below.

In another embodiment, this invention provides pharmaceutical compositions comprising the above-described inventive imidazoles as an active ingredient. The pharmaceutical compositions generally additionally comprise a pharmaceutically acceptable carrier diluent, excipient or carrier (collectively referred to herein as carrier materials). Because of their $H_1$ and $H_3$ antagonist activity, such pharmaceutical compositions possess utility in treating allergy, inflammation, nasal congestion, hypertension, glaucoma, sleeping disorders, states of hyper- and hypo-motility of the gastrointestinal tract, hypo- and hyper-activity of the central nervous system, Alzheimers, Schizophrenia, migraines, obesity and the like diseases.

In yet another embodiment, the present invention discloses methods for preparing pharmaceutical compositions comprising the inventive imidazole compounds as an active ingredient. In the pharmaceutical compositions and methods of the present invention, the active ingredients will typically be administered in admixture with suitable carrier materials suitably selected with respect to the intended form of administration, i.e. oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Moreover, when desired or needed, suitable binders, lubricants, disintegrating agents and coloring agents may also be incorporated in the mixture. Powders and tablets may be comprised of from about 5 to about 95 percent inventive composition.

Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum and the like. Sweetening and flavoring agents and preservatives may also be included where appropriate. Some of the terms noted above, namely disintegrants, diluents, lubricants, binders and the like, are discussed in more detail below.

Additionally, the compositions of the present invention may be formulated in sustained release form to provide the rate controlled release of any one or more of the components or active ingredients to optimize the therapeutic effects, i.e. antihistaminic activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

Liquid form preparations include solutions, suspensions and emulsions. As an example may be mentioned water or water-propylene glycol solutions for parenteral injections or addition of sweeteners and pacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier such as inert compressed gas, e.g. nitrogen.

For preparing suppositories, a low melting wax such as a mixture of fatty acid glycerides such as cocoa butter is first melted, and the active ingredient is dispersed homogeneously therein by stirring or similar mixing. The molten homogeneous mixture is then poured into convenient sized molds, allowed to cool and thereby solidify.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions may take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparation is subdivided into suitably sized unit doses containing appropriate quantities of the active components, e.g., an effective amount to achieve the desired purpose.

The quantity of the inventive active composition in a unit dose of preparation may be generally varied or adjusted from about 1.0 milligram to about 1,000 milligrams, preferably from about 1.0 to about 950 milligrams, more preferably from about 1.0 to about 500 milligrams, and typically from about 1 to about 250 milligrams, according to the particular application. The actual dosage employed may be varied depending upon the patient's age, sex, weight and severity of the condition being treated. Such techniques are well known to those skilled in the art.

Generally, the human oral dosage form containing the active ingredients can be administered 1 or 2 times per day. The amount and frequency of the administration will be regulated according to the judgment of the attending clinician. A generally recommended daily dosage regimen for oral administration may range from about 1.0 milligram to about 1,000 milligrams per day, in single or divided doses.

Capsule—refers to a special container or enclosure made of methyl cellulose, polyvinyl alcohols, or denatured gelatins or starch for holding or containing compositions comprising the active ingredients. Hard shell capsules are typically made of blends of relatively high gel strength bone and pork skin gelatins. The capsule itself may contain small amounts of dyes, opaquing agents, plasticizers and preservatives.

Tablet—refers to a compressed or molded solid dosage form containing the active ingredients with suitable diluents. The tablet can be prepared by compression of mixtures or granulations obtained by wet granulation, dry granulation or by compaction.

Oral gels—refers to the active ingredients dispersed or solubilized in a hydrophillic semi-solid matrix.

Powders for constitution refers to powder blends containing the active ingredients and suitable diluents which can be suspended in water or juices.

Diluent—refers to substances that usually make up the major portion of the composition or dosage form. Suitable diluents include sugars such as lactose, sucrose, mannitol and sorbitol; starches derived from wheat, corn, rice and potato; and celluloses such as microcrystalline cellulose. The amount of diluent in the composition can range from about 10 to about 90% by weight of the total composition, preferably from about 25 to about 75%, more preferably from about 30 to about 60% by weight, even more preferably from about 12 to about 60%.

Disintegrants—refers to materials added to the composition to help it break apart (disintegrate) and release the medicaments. Suitable disintegrants include starches; "cold water soluble" modified starches such as sodium carboxymethyl starch; natural and synthetic gums such as locust bean, karaya, guar, tragacanth and agar; cellulose derivatives such as methylcellulose and sodium carboxymethylcellulose; microcrystalline celluloses and cross-linked microcrystalline celluloses such as sodium croscarmellose; alginates such as alginic acid and sodium alginate; clays such as bentonites; and effervescent mixtures. The amount of disintegrant in the composition can range from about 2 to about 15% by weight of the composition, more preferably from about 4 to about 10% by weight.

Binders—refers to substances that bind or "glue" powders together and make them cohesive by forming granules, thus serving as the "adhesive" in the formulation. Binders add cohesive strength already available in the diluent or bulking agent. Suitable binders include sugars such as sucrose; starches derived from wheat, corn rice and potato; natural gums such as acacia, gelatin and tragacanth; derivatives of seaweed such as alginic acid, sodium alginate and ammonium calcium alginate; cellulosic materials such as methylcellulose and sodium carboxymethylcellulose and hydroxypropylmethylcellulose; polyvinylpyrrolidone; and inorganics such as magnesium aluminum silicate. The amount of binder in the composition can range from about 2 to about 20% by weight of the composition, more preferably from about 3 to about 10% by weight, even more preferably from about 3 to about 6% by weight.

Lubricant—refers to a substance added to the dosage form to enable the tablet, granules, etc. after it has been compressed, to release from the mold or die by reducing friction or wear. Suitable lubricants include metallic stearates such as magnesium stearate, calcium stearate or potassium stearate; stearic acid; high melting point waxes; and water soluble lubricants such as sodium chloride, sodium benzoate, sodium acetate, sodium oleate, polyethylene glycols and d'l-leucine. Lubricants are usually added at the very last step before compression, since they must be present on the surfaces of the granules and in between them and the parts of the tablet press. The amount of lubricant in the composition can range from about 0.2 to about 5% by weight of the composition, preferably from about 0.5 to about 2%, more preferably from about 0.3 to about 1.5% by weight.

Glidents—materials that prevent caking and improve the flow characteristics of granulations, so that flow is smooth and uniform. Suitable glidents include silicon dioxide and talc. The amount of glident in the composition can range from about 0.1% to about 5% by weight of the total composition, preferably from about 0.5 to about 2% by weight.

Coloring agents—excipients that provide coloration to the composition or the dosage form. Such excipients can include food grade dyes and food grade dyes adsorbed onto a suitable adsorbent such as clay or aluminum oxide. The amount of the coloring agent can vary from about 0.1 to about 5% by weight of the composition, preferably from about 0.1 to about 1%.

Bioavailability—refers to the rate and extent to which the active drug ingredient or therapeutic moiety is absorbed into the systemic circulation from an administered dosage form as compared to a standard or control.

Conventional methods for preparing tablets are known. Such methods include dry methods such as direct compression and compression of granulation produced by compaction, or wet methods or other special procedures. Conventional methods for making other forms for administration such as, for example, capsules, suppositories and the like are also well known.

Another embodiment of the invention discloses use of the pharmaceutical compositions disclosed above for treatment of diseases such as, for example, allergy, inflammation, nasal congestion, hypertension, glaucoma, sleeping disorders, states of hyper- and hypo-motility of the gastrointestinal tract, hypo- and hyper-activity of the central nervous system, Alzheimers, Schizophrenia, migraines, obesity and the like. The method comprises administering a therapeutically effective amount of the inventive pharmaceutical composition to a mammalian patient having such a disease or diseases and in need of such a treatment.

Those skilled in the art will realize that the term "upper airway" means the upper respiratory system—i.e., the nose, throat, and associated structures.

It will be apparent to those skilled in the art that many modifications, variations and alterations to the present disclosure, both to materials and methods, may be practiced. Such modifications, variations and alterations are intended to be within the spirit and scope of the present invention.

The following EXAMPLES are being provided to further illustrate the present invention. They are for illustrative purposes only; the scope of the invention is not to be considered limited in any way thereby.

EXAMPLES

Unless otherwise stated, the following abbreviations have the stated meanings in the Examples below:

DBU=1,8-diazabicyclo[5.4.0]undec-7-ene
DBN=1,5-diazabicyclo[4.3.0]non-5-ene
EDCI=1-(3-dimethylaminopropyl)-3-ethylcarbodiimide
HOBT=1-hydroxybenzotriazole
DCC=dicyclohexylcarbodiimide
Dibal-H=diisobutylaluminum hydride
LAH=lithium aluminum hydride
NaBH(OAc)$_3$=sodium triacetoxyborohydride NaBH₄=sodium borohydride
NaBH₃CN=sodium cyanoborohydride
LDA=lithium diisopropylamide
p-TsOH=p-toluenesulfonic acid
m-CPBA=m-Chloroperbenzoic acid
TMAD=N, N, N', N'-tetramethylazod icarboxamide
CSA=camphorsulfonic acid
NaHMDS=sodium hexamethyl disilylazide
HRMS=High Resolution Mass Spectrometry
HPLC=High Performance Liquid Chromatography
LRMS=Low Resolution Mass Spectrometry
nM=nanomolar
Ki=Dissociation Constant for substrate/receptor complex
pA2=-logEC₅₀, as defined by J. Hey, *Eur. J. Pharmacol.,* (1995), Vol. 294, 329–335.
Ci/mmol=Curie/mmol ( a measure of specific activity)
Tr=Triphenylmethyl
Tris=Tris(hydroxymethyl)aminomethane Example 1. Preparation of compound (1)

The aldehyde made from urocanic acid (procedure disclosed in WO 96/38142, published Dec. 5, 1996) was tritylated according to literature procedure (Kelley, *J. Med. Chem.* 20(5), 721 (1977)) to afford compound (1).

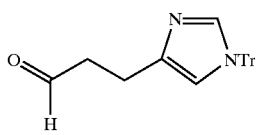

Example 2. Preparation of compound (4)

(i) Preparation of compound (3).

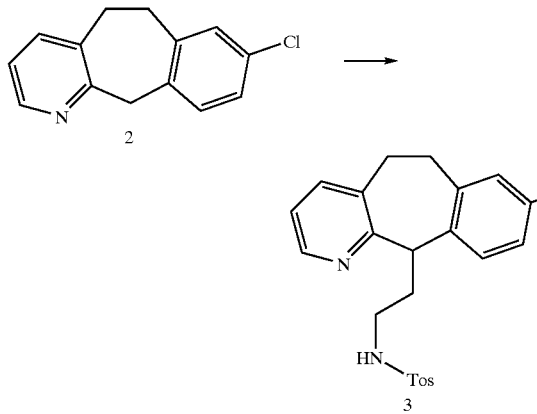

The literature compound (2) (Villani et al. *J. Med. Chem.,* (1972) 15 750) was converted to the tosylate (3) according to the literature procedure (Afonso et al. *Tetrahedron Lett.,* (1998) 39 7661–7664).

(ii) Preparation of compound (4).

The tosylate (3) (1 g) was combined with 48% HBr (10 ml) and phenol (1 g) and heated to 120° C. for 8 h. The reaction was then diluted with ice/water (20 ml) and washed with CH₂Cl₂. The aqueous layer was

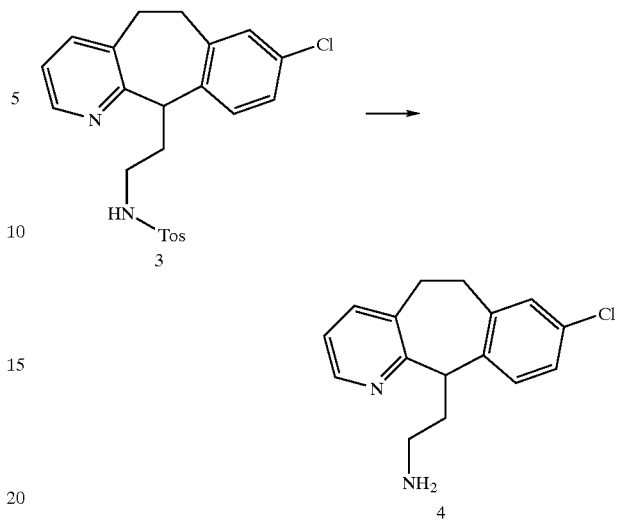

basified with 10% NaOH to pH=10 then extracted with CH₂Cl₂. The organic layers were combined dried over MgSO₄ and concentrated to afford the title compound (4) as a gummy solid.

Example 3. Preparation of compounds (5) and (6)

Compound (1) (0.423 g) was dissolved in MeOH (4 ml ), a solution of compound (4) (0.314 g) in MeOH (2 ml) was added and the resulting mixture cooled in an ice bath. To the solution was then added Na(OAc)₃BH (0.486 g) portionwise. After standing for 2 days in the refrigerator, the mixture was diluted with water and extracted with CH₂Cl₂. The organic layer was washed with dilute HCl, then brine and concentrated. The crude product mixture was purified by flash silica column chromatography eluting

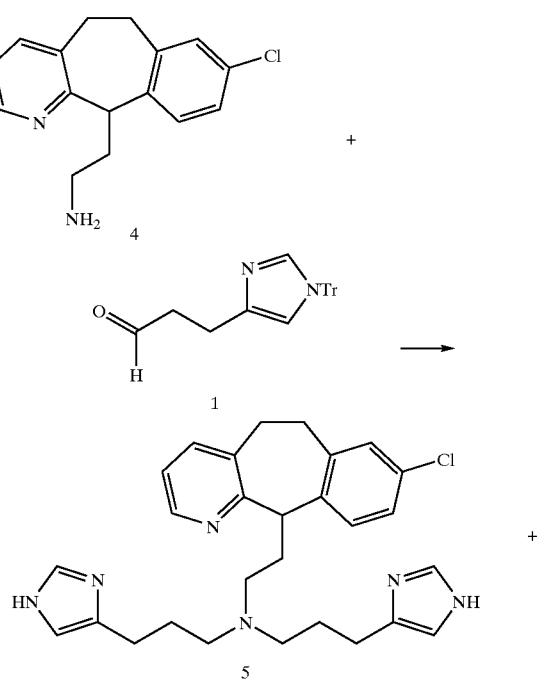

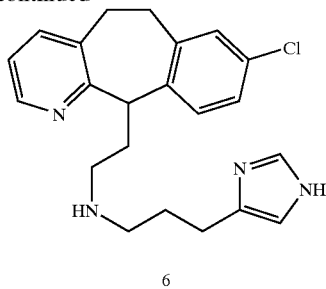

6 with MeOH:NH$_4$OH: CH$_2$Cl$_2$ (10:2:88) affording both the secondary and tertiary amines. The amines were separately detritylated by treating with 1 N HCl in EtOH (20 mL) and heating to 60° C. for 1 h. The reactions were concentrated and then diluted with water. The white solids that had formed were removed by filtration. The filtrates were washed with ether and the aqueous layers concentrated to give the title compounds (5) and (6).

Example 4. Preparation of ω-[1-(triphenylmethyl)-1H-imidazol-4-yl]-butanal (10)

(i) Preparation of 1-(triphenylmethyl)-1H-imidazol-4-carboxaldehyde (7):

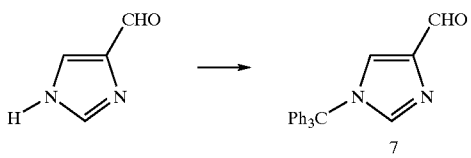

To a stirred suspension of 4-imidazole carboxaldehyde (from Maybridge Chemicals, United Kingdom) (35.0 g, 364 mmol) and triethylamine (55.8 mL; 400 mmol) in dichloromethane (2 L), was added a solution of triphenylmethyl chloride in dichloromethane (600 mL) while maintaining the reaction temperature at approximately 15° C. with a cooling bath. The resultant solution was warmed to room temperature and stirred for 19 h. Washed the reaction solution with a solution of saturated brine and water (1:3.5; 3×600 mL), followed by brine (1×800 mL). Dried over sodium sulfate; filtered to remove drying agent; and removed solvent under vacuum to obtain the desired tritylated product (7) as an off-white solid. MP 186.5–194° C. [Trituration of this product with ether yielded a cream-colored powder with mp 195–197° C.]

(ii). Preparation of 4-[(Z)-4-(phenylmethoxy)-1-butenyl]-1-(triphenylmethyl)-1H-imidazole (8):

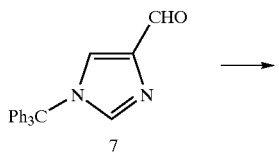

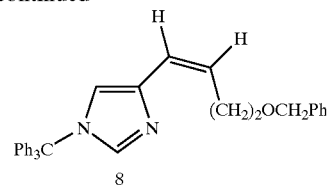

To a mechanically-stirred solution of the aldehyde (7) (from 4 (i) above) in dry tetrahydrofuran (1 L), was added (3-benzyloxypropyl)triphenyl phosphonium bromide (30.02 g, 61.1 mmol). Cooled the resulting suspension to 15° C., and over five minutes added a 1.0 M solution (61.4 mL; 614 mmol) of potassium t-butoxide in tetrahydrofuran. Allowed the reaction mixture to warm to room temperature and stirred for 2 h. Filtered the reaction mixture through Celite; washed the filter cake with tetrahydrofuran (2×150 mL); combined filtrate and washings and diluted with ether (800 mL); refiltered through fresh Celite. Concentrated the filtrate under vacuum, and chromatographed the residue on silica gel, eluting with a gradient of hexanes-ethyl acetate (3:1->2:1), to obtain the title compound (8). mp 101–104° C. MS(FAB) 471 (MH$^+$).

(iii). Preparation of 1-(triphenylmethyl)-1H-imidazole-4-butanol (9):

Hydrogenated a mixture of the olefinic ether (8) from 4 (ii) above, (18.27 g, 38.8 mmol) in anhydrous methanol (350 mL), 1.0 M ethereal hydrochloric acid (38.8 mL, 38.8 mmol) and 10% palladium-on-carbon catalyst at 48 psi for 30 min. on a Parr shaker. Filtered through celite and

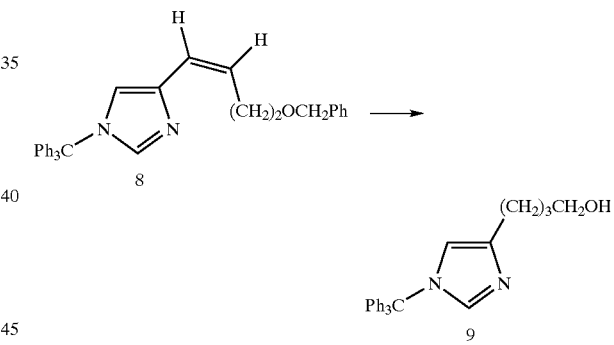

washed the filter cake with methanol. Concentrated the combined filtrate and washings, and dried under high vacuum to obtain the title compound (9) as an off-white solid. MP 144–146° C.

(iv). Preparation of ω-[1-(triphenylmethyl)-1H-imidazol-4-yl]-butanal (10):

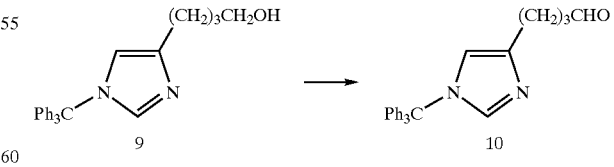

In a dry flask equipped to provide an inert gas atmosphere, prepared a solution of oxalyl chloride (2.18 mL, 25.0 mmol) in dry dichloromethane (50 mL) and cooled to −60° C. in a CO$_2$-acetone bath. Added dropwise over 5–10 min. a solution of dimethylsulfoxide (3.60 mL, 50.7 mmol) in dry dichloromethane (10 mL), while maintaining the reaction temperature at −55 to −60° C. Stirred an additional 5 min at −60° C.; then added a solution of compound (9) (8.67 g, 20.7 mol) in dry dichloromethane (140 mL) over 15–20 minutes, maintaining reaction temperature in the range of −55 to −60° C. Continued stirring at −60° C. for one hour; then added neat triethylamine (17.6 mL; 12.6 mmol) at a rate such that the reaction temperature was maintained at −55 to −60° C. Stirred for 5 min. at this temperature. Removed the cooling bath, and continued to stir at room temperature for 1.5 h. The reaction mixture was washed with water (4×50 mL), brine (75 mL) and dried over anhydrous magnesium sulfate. The solvent was removed under vacuum to obtain a viscous oil. If triethylamine hydrochloride remained, the residual oil was dissolved in diethyl ether (100 mL), washed with water (1×30 mL; 2×10 mL), then with brine (30 mL), and dried over anhydrous magnesium sulfate. Removed solvent under vacuum to obtain the title aldehyde (10) as a viscous yellow oil, sufficiently pure for further chemistry. MS(FAB) 381 (MH$^+$).

Example 5. Preparation of ω-[1-(triphenylmethyl)-1H-imidazol-4-yl]-pentanal (14)

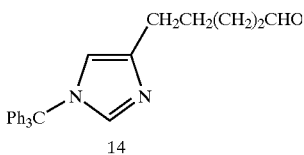

14

(i) Preparation of (ethoxycarbonylprop-1-yl)triphenyl phosphonium bromide (11):

A mixture of triphenylphosphine (24.6 g; 0.0936 mol) and ethyl 4-bromobutyrate (from Aldrich Chemical Company, Milwaukee, Wis.) (14.4 mL; 0.101 mol) was heated from room temperature to 105° C. over a period of 15–20 minutes, and continued heating the resultant solution at 105° C. for 10 minutes. Allowed the solution to cool, but while still warm cautiously added diethyl ether (50 mL) via a condenser. Triturated the resultant gum to obtain a white powder. Decanted, added fresh diethyl ether (50 mL), and continued trituration for 10 min. Filtered the reaction mixture; washed the filter cake with diethyl ether; and under vacuum removed solvent from the combined filtrate and washings to obtain a mixture of oil and solids. Heated this mixture to 100° C.; cautiously treated with diethyl ether (2×55 mL); and repeated the trituration, filtration, and concentration sequence described above. Combined the two batches of white solids obtained from this process, triturated with toluene (150 mL), filtered, washed the collected solids with toluene and dried under high vacuum to obtain the title salt (11). FABMS 377 (M$^+$) mp 177–179° C.

(ii) Preparation of ethyl 5-[1-(triphenylmethyl)-1H-imidazol-4-yl]-4-Z-pentenoate (12):

Under a nitrogen atmosphere, added the triphenylphosphonium salt (11) (from 5(i) above) (14.0 g, 0.0305 mol) to a stirred solution of aldehyde (7) (from 4(i) above) (9.81 g, 0.029 mol) in tetrahydrofuran (500 mL). Cooled the resultant suspension to 0–5° C., added 1 M potassium t-butoxide in tetrahydrofuran (31 mL, 0.031 mol) over 3–5 min., stirred the mixture for 20 min. at 0–5° C. Added Celite to the reaction mixture, stirred briefly, filtered, and washed filter cake with diethyl ether, followed by dichloromethane. Concentrated the combined filtrate and washings under vacuum. Chromatographed the residual oil on silica gel. Eluted with a gradient of hexanes-ethyl acetate (3:1->2:1), to obtain the title compound (12) as a white solid. FABMS 437 (MH$^+$) mp 90–92.5° C.

(iii) Preparation of 5-[1-(triphenylmethyl)-1H-imidazol-4-yl]-4-Z-pentenal (13):

To a stirred cooled (about −55° C.) solution of the ester compound (12) (671 mg, 1.54 mmol) in dry dichloromethane (12 mL) contained in a cold bath, was added a 1.0 M solution of DIBAL-H in toluene (3.08 mL, 3.08 mmol) over approximately 4 min., while maintaining the reaction temperature at −55 to −60° C. After 8–10 min. of stirring at −58° C., quenched the reaction by the addition of methanol (0.4 mL) and water (6 mL). Allowed the reaction mixture to warm to room temperature. Removed the gelatinous precipitate that forms by filtration through Celite. Washed the filter cake with dichloromethane, and dried the combined filtrate and washings over anhydrous magnesium sulfate. Filtered the drying agent and evaporated the solvent under reduced pressure to obtain the title aldehyde (13) as a white powder. FABMS 393 (MH$^+$) mp 117.5–120° C.

(iv) Preparation of ω-[1-(triphenylmethyl)-1H-imidazol-4-yl]-pentanal (14):

Hydrogenated a mixture of the unsaturated aldehyde (13) (5.42 g; 13.8 mmol) and 5% palladium-on-charcoal catalyst (0.50 g) in anhydrous methanol (130 mL) for 30 min. at 30–35 psi on a Parr shaker. Filtered the catalyst through Celite, evaporated the filtrate under reduced pressure and dried the residue under high vacuum to obtain the title compound (14) as a yellow viscous oil or glass sufficiently pure for further chemistry. FABMS 395 (MH$^+$).

Reacting compound (4) with aldehyde (10) in the same manner as in Example 3, the following compounds 15 (Example 6) and 16 (Example 7) were prepared:

Example 6. Compound (15)

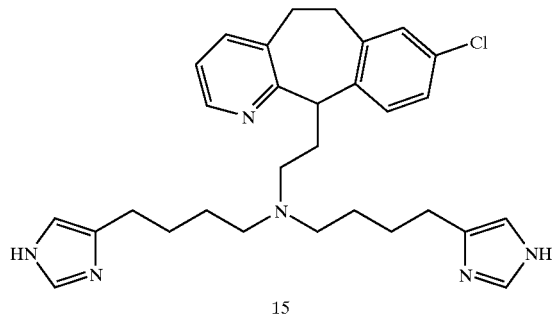

15

Example 7. Compound (16)

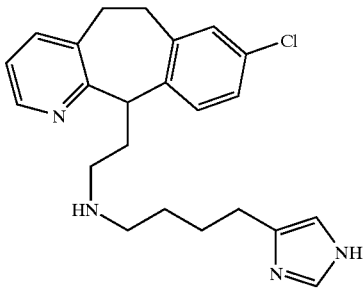

16

Reacting compound (4) with aldehyde (14) in the same manner as in Example 3, the following compounds 17 (Example 8) and 18 (Example 9) were prepared:

Example 8. Compound (17)

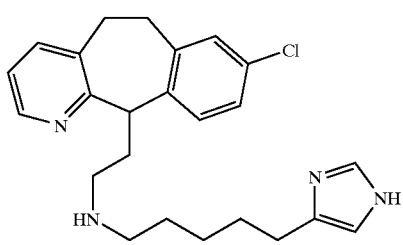

Example 9. Compound (18)

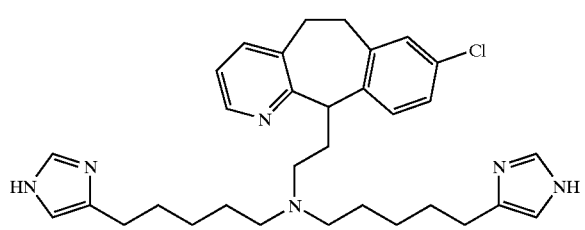

Example 10. Preparation of compound (22)

(i) Preparation of compound (20):

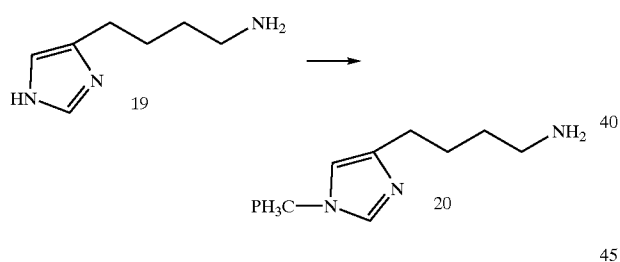

The imidazole butyl amine compound (19) (prepared by literature method: Durant, G. J. et al. JMCMAR; *J. Med. Chem.* EN, (1985) 28 (10), 1414–1422) was protected following a similar procedure as in Example 4 (i) affording the title compound (20).

(ii) Preparation of compound (22).

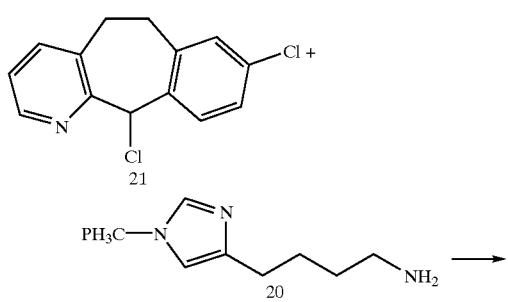

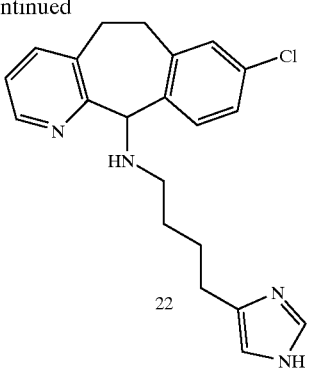

The tricyclic compound (21) disclosed in U.S. Pat. No. 5,151,423 (1992) (0.22 g) was reacted with compound (20) (0.307 g), and $Et_3N$ (0.101 g) in $CH_2Cl_2$ (5 ml) overnight at room temperature. The mixture was then diluted with $CH_2Cl_2$ and washed with 0.5 N NAOH, water then brine, dried over $MgSO_4$ and concentrated. Crude product was purified by flash silica gel column chromatography eluting with 5% $NH_3$ saturated MeOH in $CH_2Cl_2$. Pure product was detritylated in the same manner as described in Example 3 affording the title compound (22).

Example 11: Preparation of Compound 24

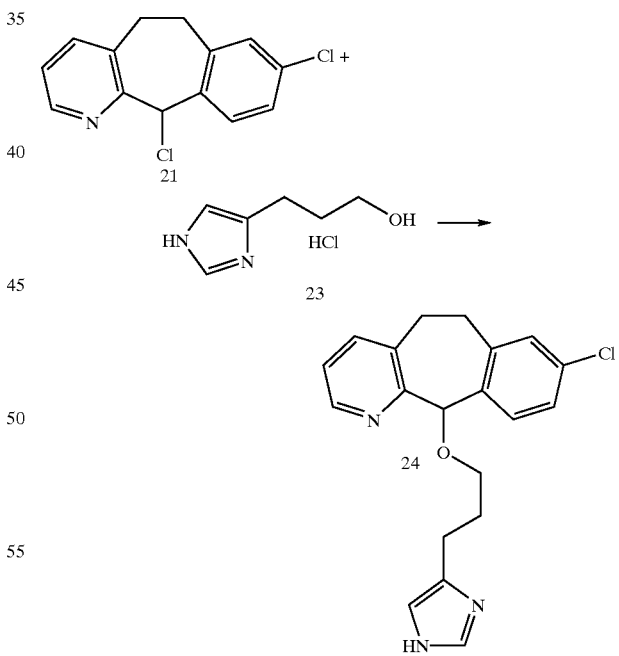

A solution of the chloride 21 (*J. Med. Chem.*, 1998, 41, 877; 1 mmol) in sufficient acetonitrile is treated with the alcohol 23 (1 mmol) according to *Bioorg. & Med. Chem. Lett.*, 1996, 6, 2013 to give the target compound 24.

Example 12: Preparation of Compound 28

(i)

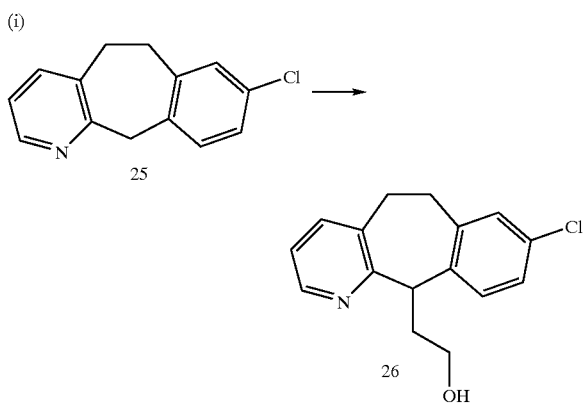

A solution of compound 25 (*Tetrahedron Lett.,* 1998, 39, 7661; 1.1 mmol) in dry THF is treated at −78° C. with LDA (1.2 mmol). It is stirred for 1 to 3 h at this temperature. A solution of ethylene oxide in sufficient THF is added and warmed to room temperature over 1–2 h. The reaction is stirred at room temperature for 1–5 h., then diluted with water and extracted with ethyl acetate. The organic layer is dried (MgSO$_4$) and concentrated. The product 26 is purified by chromatography on a silica gel column.

(ii)

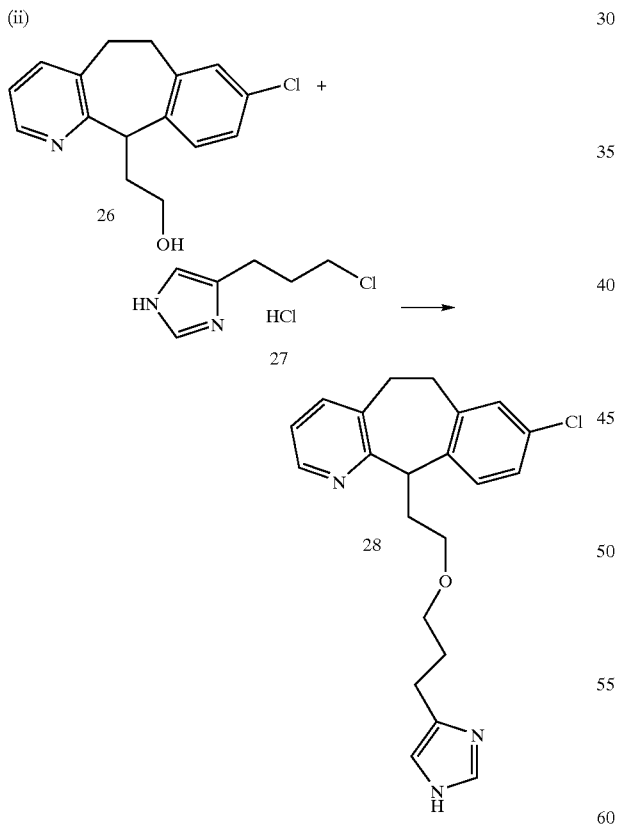

The alcohol 26 (1 mmol) is dissolved in THF, cool to 0° C., and treated with NaH (1.2 mmol). It is stirred for 1–2 h and treated with a solution of compound 27 (*J. Med. Chem.,* 28, 1414; 0.5 mmol) in sufficient THF. The cooling bath is removed and the reaction stirred at room temperature for 1–10 h, then diluted with water and the product is extracted into ethyl acetate. The organic layer is dried (MgSO$_4$) and purified on a silica gel column to yield compound 28.

Example 13: Synthesis of sulfide 30

(i) Preparation of Compound 29 from compound 26:

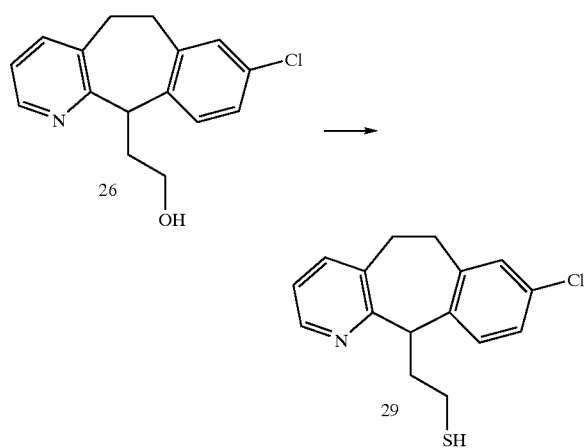

Compound 26 (1 mmol) is dissolved in concentrated HCl and to it thiourea (1.5 mmol) is added. It is heated to 75° C. for 1–10 h., then cooled to 0° C. in an ice bath and neutralized with 1 N NaOH. It is extracted with ethyl acetate, the organic layer dried (MgSO$_4$), concentrated, and the residue is purified on a silica gel column. The residue is dissolved in sufficient ethanol and treated with 5 N KOH. It is heated to 65° C. for 1–10 h under a nitrogen atmosphere, then cooled to 0° C. in an ice bath and neutralized with 1N HCl. It is extracted with ethyl acetate, the organic layer dried (MgSO$_4$), concentrated, and residue purified on a silica gel column to give compound 29.

(ii)

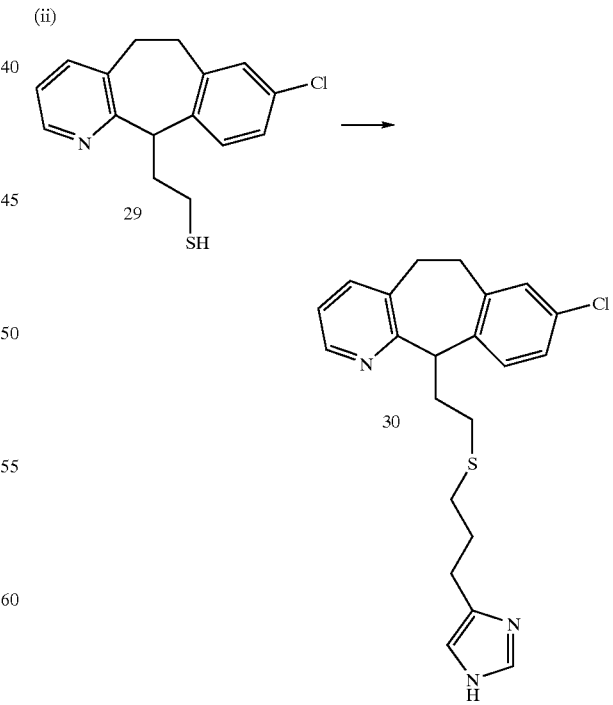

In a similar manner to that described in Example 12, Step 2, compound 29 is converted to 30.

Example 14. Preparation of Compound 31

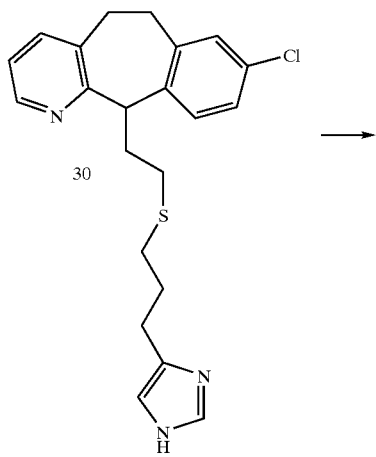

30

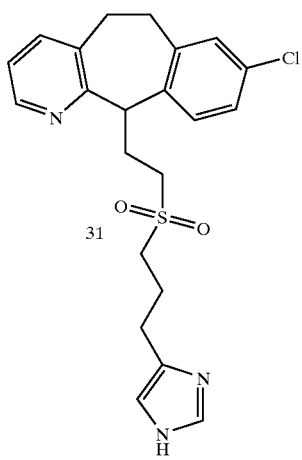

31

An aqueous solution of oxone (3 mmol in 3 mL of water) is slowly added to a solution of compound 30 (1 mmol) in methanol (3 mL) at 20° C. It is stirred for 1–6 h., methanol is removed in vacuo and the aqueous layer extracted twice with ethyl acetate. The organic layer is dried (MgSO$_3$) and concentrated. The residue is purified on a silica gel column to give the product 31.

Example 15. Preparation of the Compound 33

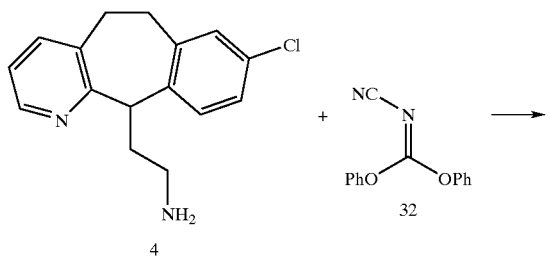

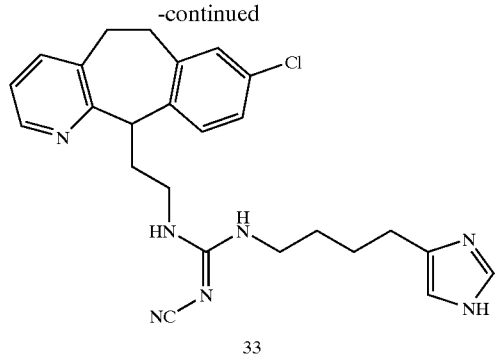

33

A solution of 32 (1 mmol) in acetonitrile is treated at 20° C. with amine 4 in acetonitrile and stirred for 1–10 h. Compound 4 in acetonitrile is added and the reaction is heated to reflux for 1–10 h., cooled and concentrated, then diluted with water and extracted into ethyl acetate. The organic layer is dried (MgSO$_4$), concentrated, and the residue purified on a silica gel column to yield compound 33.

In a similar manner, the following compounds may be prepared:

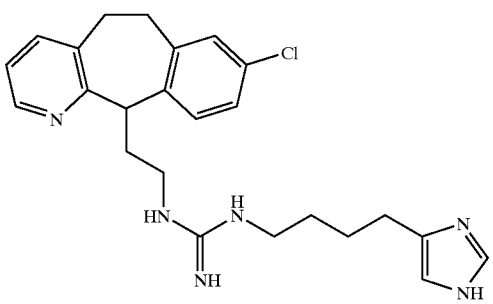

34

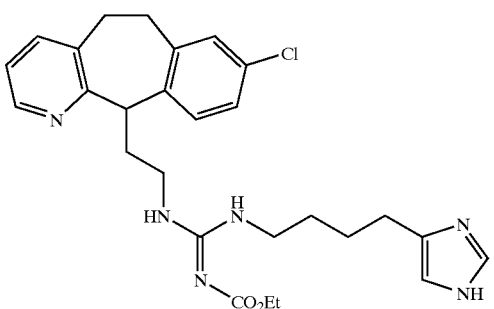

35

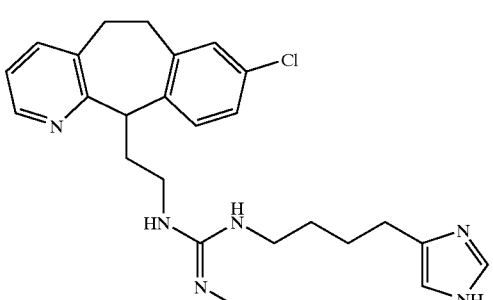

36

-continued

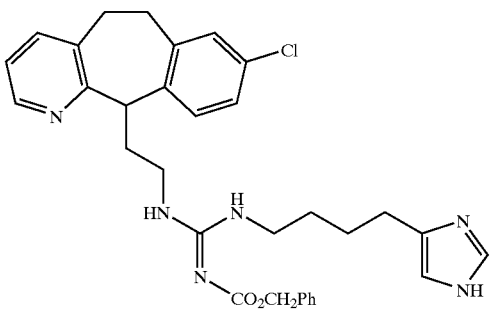

37

Example 16. Preparation of the Compound 38

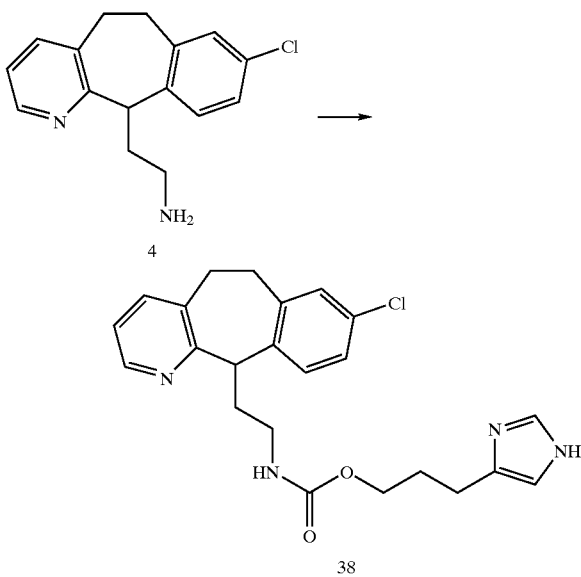

A solution of trichloromethyl chloroformate (1.25 mmol) in dry ethyl acetate is treated at 20° C. with a small amount of charcoal followed by addition of the amine 4 (1 mmol) in dry ethyl acetate. The mixture is stirred for 5 min and then heated to reflux, then cooled, filtered, and concentrated in vacuo. The residue is dissolved in dry acetonitrile and alcohol 23 is added. The mixture is refluxed for 1–10 h., cooled and concentrated. The residue is purified by silica gel chromatography to yield compound 38.

General Procedure for H1.—Receptor Binding Assay: The procedure used was based on that disclosed in V. T. Tran et al, "Histamine $H_1$ receptors identified in mammalian brain membranes with [H-3]mepyramine", Proc. Natl. Acad. Sci. U.S.A. 75 (1978) 6290–6294.

I. Tissue preparation protocol for histamine $H_1$ receptor binding assay:

1. The tissue source was male Sprague-Dawley rat brain. These were purchased stripped and frozen (available from Rockland Corporation, Gilbertsville, Pa.). The buffer used was ice-cold 50 mM Tris-HCl, pH 7.5. (The pH was determined at 25° C.)

2. The brains were spread out on plastic wrap on the benchtop and allowed to thaw for 10–15 min. After this, everything was kept ice-cold.

3. Two brains were put in each 50 ml round bottom centrifuge tube and 25 ml of buffer was added. Then they were broken up with a Polytron (from Brinkmann Instruments, Westbury, N.Y.) equipped with a PT-10 tip at setting 6 for 30 sec.

4. The volume in the tube was brought up to 45 ml and mixed and the particulate material was centrifuged at 1000×g (3000 rpm, SS-34 rotor) for 10 min to remove nuclei and unbroken cells.

5. Pellets were discarded and the supernatants were centrifuged 10 min at 50,000×g (20,000 rpm, SS-34 rotor).

6. The high-speed pellets were resuspended in a volume of Tris buffer equal to the original (4 ml), the contents of all tubes were pooled, and a sample was taken for BCA protein assay . The material was aliquotted, 45 ml per round-bottom tube, and the resuspension was recentrifuged. The yield of protein was approximately 20 mg/brain, so there was about 40 mg of protein per tube.

7 . Pellets were frozen at −80° C.

II. $H_1$ Histamine receptor binding assay:

Materials: 96-well, deep-well, polypropylene plates, [$^3$H] pyrilamine, 20–30 Ci/mmol, from Dupont NEN Life Science Products, Boston, Mass.), chlorpheniramine maleate (from Schering-Plough Corporation, Kenilworth, N.J.) as standard, stored as frozen $10^{-5}$, $10^{-6}$, $10^{-7}$, $10^{-8}$ M solutions.

1. FDCL and comparative compounds for assay were independently solubilized at 1 mg/ml DMSO by vortexing, or if necessary by sonication. The first dilution, 100-fold, was made in 50 mM Tris-HCl, pH 7.5, at room temperature. The three or four subsequent ten-fold serial dilutions were made in 1% DMSO/50 mM Tris-HCl, pH 7.5. Drug solutions and assay plates were kept at room temperature during the course of the assay set up.

2. Test compounds were assayed at four or five concentrations: 1, 0.1, 0.01, 0.001, and 0.0001 μg/ml. Twenty μl of drug solution was pipeted into each of three wells. A chlorpheniramine maleate standard was assayed at $10^{-9}$ to $10^{-6}$ M, 20 μl of each of the appropriate solutions being pipeted into triplicate wells. Total and nonspecific ($10^{-6}$ M chlorpheniramine maleate) binding were determined at least in quadruplicate. For total binding, 20 μl of buffer was pipeted and for nonspecific 20 μl of $10^{-5}$ M chlorpheniramine maleate was pipeted into each well.

3. [$^3$H]Pyrilamine was diluted approximately 2000-fold with ice-cold mM Tris-HCl, pH 7.5 (to a working concentration of 20–25 nM), and put on ice.

4. A frozen tissue pellet was thawed in a 25° C. water bath, resuspended in 50 mM Tris-HCl, pH 7.5, at 1.7–2 mg/ml by brief break-up on the Polytron, and put on ice.

5. Twenty μl of diluted [$^3$H]pyrilamine was added to each well.

6. One hundred fifty μl of tissue suspension was added to each well.

7. The top of the plate was covered and it was placed in a 25° C. shaking water bath (about 60 oscillations/min) for 30 min..

8. Samples were filtered on a Tomtec Mach 2 harvester (available from Tomtec Corporation, Orange, Conn.) through a GF/B filter mat (from Wallac, Inc., Gaithersburg, Md.) presoaked in 0.3% polyethylenimine. Each sample was thrice washed with ice-cold 50 mM Tris-HCl, pH 7.5 dried 20 sec on the Tomtec, and dried 3–4 min in a microwave oven on a paper towel. The filter was impregnated with MELTILEX brand wax scintillant (from Wallac Corporation) and counted on a Betaplate scintillation counter (from Wallac Corporation).

9. Specific binding was determined as the difference between total and nonspecific binding. The percent inhibition in the presence of inhibitor or standard was determined using the formula: [1-(sample binding-nonspecific binding)/specific binding]×100 For compounds that inhibit more than 50% at 1 µg/ml, an $IC_{50}$ value was interpolated from proximate concentrations. The value was converted to a nM value using the compound formula weight and a $K_i$ value was calculated using the equation of Cheng and Prusoff ($K_i = IC_{50}/(1+[L]/K_D)$), [Y-C. Cheng and W. H. Prusoff, "Relationship between the inhibitory constant ($K_i$) and the concentration of inhibitor which causes 50 per cent inhibition ($IC_{50}$) of an enzymatic reaction", *Biochem. Pharmacol.* 22 (1973) 3099–3108]. Lower value of $K_i$ indicates greater binding affinity.

General Procedure for $H_3$—Receptor Binding Assay

The source of the $H_3$ receptors in this experiment was guinea pig brain. The animals weighed 400-600 g. The brain tissue was homogenized with a solution of 50 mM Tris, pH 7.5. The final concentration of tissue in the homogenization buffer was 10% w/v. The homogenates were centrifuged at 1,000×g for 10 min. in order to remove clumps of tissue and debris. The resulting supernatants were then centrifuged at 50,000×g for 20 min. in order to sediment the membranes, which were next washed three times in homogenization buffer (50,000×g for 20 min. each). The membranes were frozen and stored at −70° C. until needed.

All compounds to be tested were dissolved in DMSO and then diluted into the binding buffer (50 mM Tris, pH 7.5) such that the final concentration was 2 µg/ml with 0.1% DMSO. Membranes were then added (400 µg of protein) to the reaction tubes. The reaction was started by the addition of 3 nM [$^3$H]R-α-methyl histamine (8.8 Ci/mmol) or 3 nM [$^3$H]N$^α$-methyl histamine (80 Ci/mmol) and continued under incubation at 30° C. for 30 min. Bound ligand was separated from unbound ligand by filtration, and the amount of radioactive ligand bound to the membranes was quantitated by liquid scintillation spectrometry. All incubations were performed in duplicate and the standard error was always less than 10%. Compounds that inhibited more than 70% of the specific binding of radioactive ligand to the receptor were serially diluted to determine a $K_i$ (nM). The results are given in the Table 1 for the HCl salt of the indicated compound.

TABLE 1

| STRUCTURE | $H_3$ Ave $K_i$ (nM) | $H_1$ Ave $K_i$ (nM) |
|---|---|---|
| 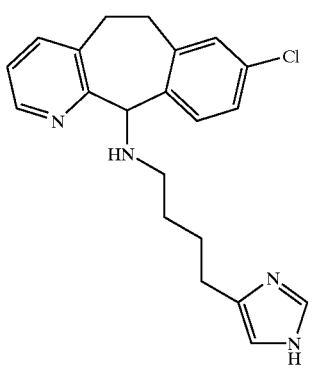 | 29 | 41 |
| 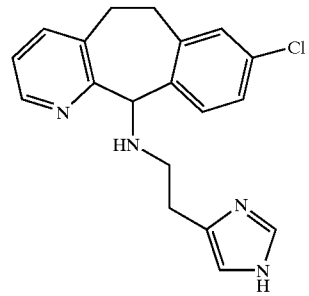 | 70 | 144 |

TABLE 1-continued

| STRUCTURE | H$_3$ Ave K$_i$ (nM) | H$_1$ Ave K$_i$ (nM) |
|---|---|---|
| 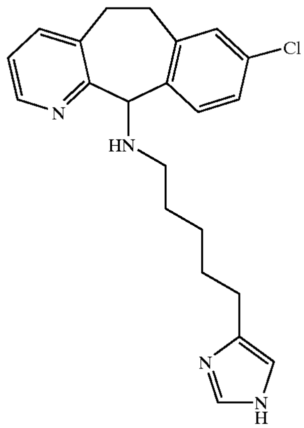 | 7.5 | 502 |
| 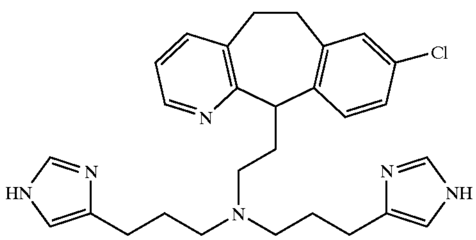 | 25 | 571 |
| 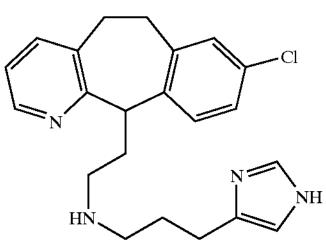 | 37 | 40 |
| 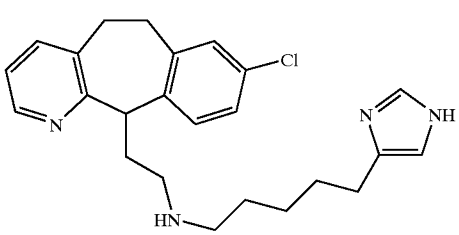 | 7 | |

TABLE 1-continued
| STRUCTURE | H₃ Ave K_i (nM) | H₁ Ave K_i (nM) |
|---|---|---|
| 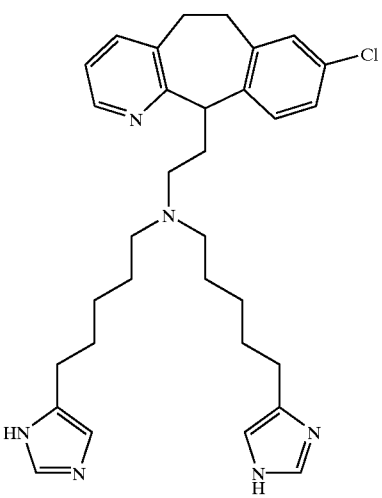 | 26 | |
| 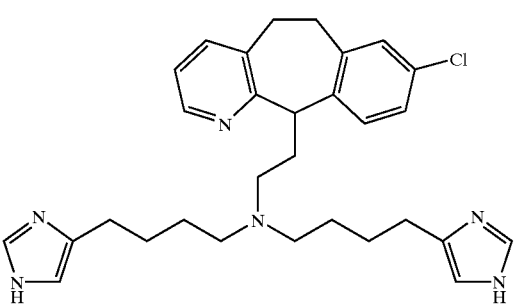 | 9 | |
| 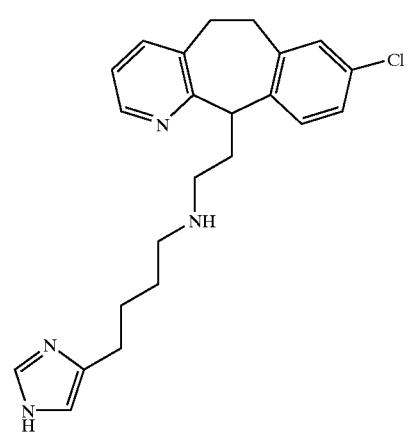 | 7.5 | |

From these test results and the background knowledge about the compounds described in the references in the section "Background of the Invention", it would be apparent to the skilled artisan that the compounds of the invention have utility in treating inflammation, allergy, diseases of the GI-tract, cardiovascular disease, disturbances of the central nervous system and the like diseases stated earlier.

What is claimed is:

1. A compound, or enantiomers, stereoisomers or tautomers thereof, or pharmaceutically acceptable salts or solvate of said compound, said compound having the general structure shown in Formula I:

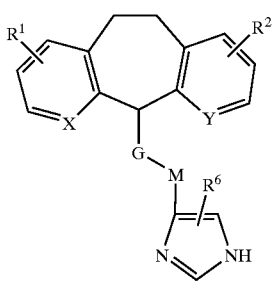

Formula 1 wherein
one of X or Y is N or N-oxide, and the other is —CH;
G is selected from the group consisting of —(CH$_2$)$_v$—NR$^3$—, —(CH$_2$)$_v$—O—, —(CH$_2$)$_v$—S(O)$_z$—, —(CH$_2$)$_v$—NR$^3$—C(NR$^4$)—NR$^3$—, —(CH$_2$)$_v$—O—C(O)NR$^3$—, —(CH$_2$)$_v$—NR$^3$C(O)NR$^3$—, —(CH$_2$)$_v$—NR$^3$C(O)O—, —(CH$_2$)$_v$—NR$^3$C(O)—, —(CH$_2$)$_v$C(O)NR$^3$—;
M is a branched or unbranched alkyl group consisting of 1–6 carbon atoms, or a branched or unbranched alkenyl group consisting of 2–6 carbon atoms;
X and Y are independently selected from the group consisting of N, CH or N-oxide;
R$^1$ and R$^2$ may each number 1–3 and are independently selected from the group consisting of H, halogen, lower alkyl, lower alkoxy, polyhalo lower alkoxy, OH, CF$_3$, NH$_2$, NHC(O)alkyl, CN or NO$_2$;
R$^3$ is independently selected from the group consisting of H, lower alkyl, substituted or unsubstituted phenyl, substituted or unsubstituted benzyl, or a group of the formula:

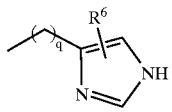

R$^4$ is selected from the group consisting of H, CN, CO$_2$R$^5$;
R$^5$ is selected from the group consisting of lower alkyl and substituted or unsubstituted benzyl;
R$^6$ is selected from the group consisting of H or lower alkyl;
q is 2–5;
v is 0–6; and
z is 0, 1 or 2.

2. The compound of claim 1, wherein R$_1$ and R$_2$ are independently selected from H, halogen, hydroxy or lower alkoxy.

3. The compound of claim 2, wherein R$^6$ is H.

4. The compound of claim 1, wherein X is N and Y is CH.

5. The compound of claim 3, wherein G is —(CH$_2$)$_v$—NR$^3$—, wherein v and R$^3$ are as defined.

6. The compound of claim 1, wherein M is an alkyl group containing 1–6 carbon atoms.

7. The compound of claim 3, wherein G is —(CH$_2$)$_v$—NR$^3$— and M is an alkyl group containing 1–6 carbon atoms, where R$^3$ and v are as defined.

8. The compound of claim 1, where X is N, Y is CH, R$^1$ is H, R$^2$ is Cl, and R$^6$ is H.

9. The compound of claim 1, wherein G is —(CH$_2$)$_v$—NR$^3$—, M is an alkyl group containing 1–6 carbon atoms, R$^1$ is H, R$^2$ is Cl, and R$^6$ is H, wherein R$^3$ and v are as defined.

10. The compound of claim 9 wherein R$^3$ is H or

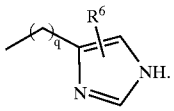

11. The compound of claim 10, wherein v is 0.

12. A composition comprising a compound of claim 1.

13. A pharmaceutical composition for use in treating inflammation, allergy, allergic rhinitis, congestion, or allergy-induced airway responses, said composition comprising as an active ingredient a compound of claim 1.

14. The composition of claim 12, additionally comprising a pharmaceutically acceptable carrier.

15. A method of treating inflammation, allergy, congestion, or allergy-induced airway responses, said method comprising administering to a mammalian patient in need of such treatment a pharmaceutical composition which comprises therapeutically effective amounts of a compound of claim 1.

16. A method of preparing a pharmaceutical composition for treating inflammation, allergy, allergic rhinitis, congestion, or allergy-induced airway responses, said method comprising bringing into intimate contact a compound of claim 1 and a pharmaceutically acceptable carrier.

17. A compound exhibiting H$_3$ antagonist activity, or enantiomers, stereoisomers or tautomers of said compound, or pharmaceutically acceptable salts or solvate of said compound, said compound being selected from the compounds of structures listed below:

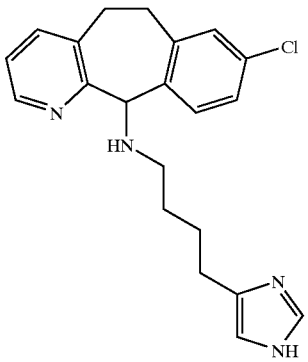

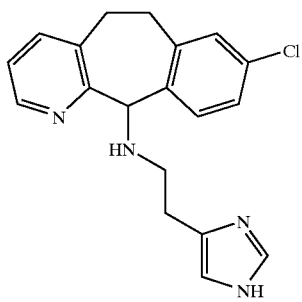
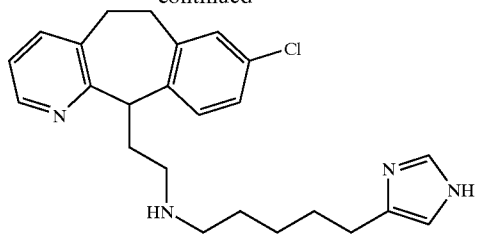
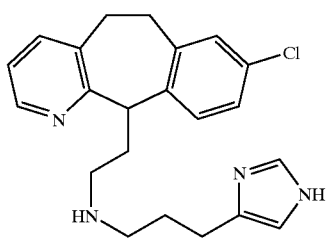
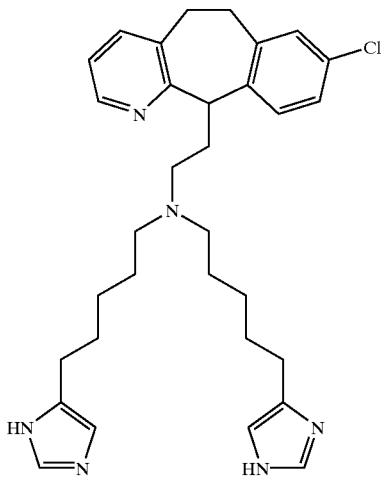
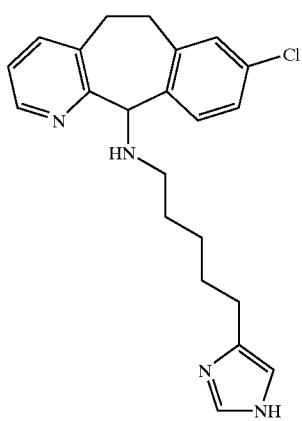
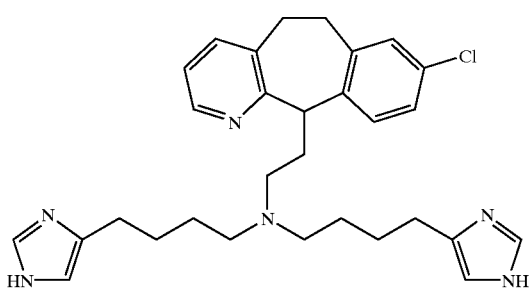
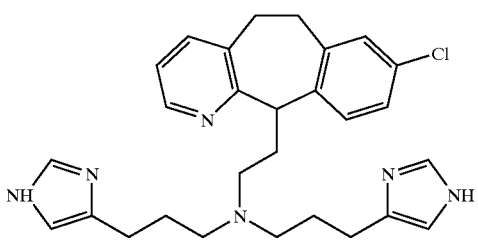
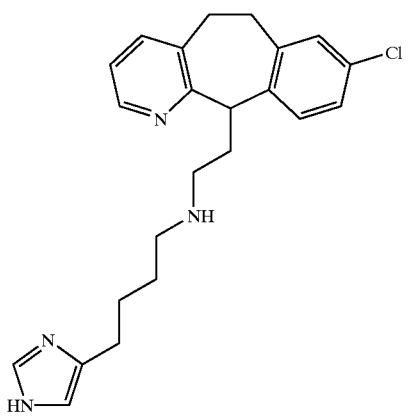

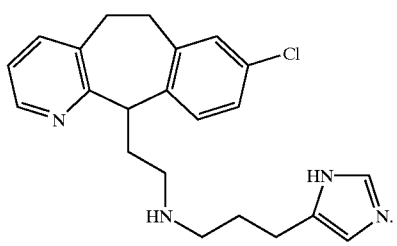

18. A compound exhibiting both $H_1$ and $H_3$ antagonist activity, or enantiomers, stereoisomers or tautomers of said compound, or pharmaceutically acceptable salts or solvate of said compound, said compound being selected from the compounds of structures listed below:

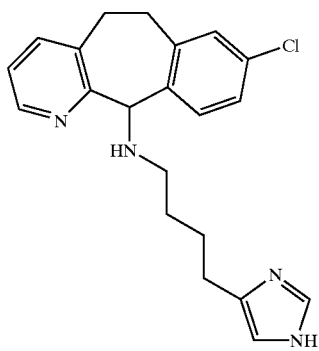

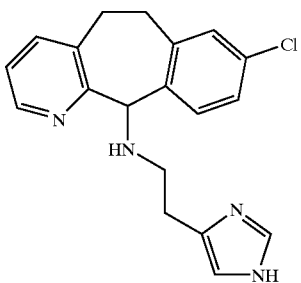

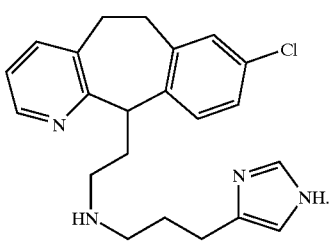

19. A pharmaceutical composition for treating inflammation, allergy, allergic rhinitis, congestion, or allergy-induced airway responses, said composition comprising therapeutically effective amount of a compound of claim 18 and a pharmaceutically acceptable carrier.

* * * * *